United States Patent [19]

Schmierer

[11] Patent Number: 4,925,958

[45] Date of Patent: May 15, 1990

[54] PROCESS FOR THE PREPARATION OF N-ALKOXYCARBONYLMETHYL-N-FORMYL-AMINES AND -ANILINES

[75] Inventor: Roland Schmierer, Todtenweis, Rudolf Kunstmann, Aystetten, both of Fed. Rep. of Germany

[73] Assignee: Hoechst Aktiengesellschaft, Frankfurt am Main, Fed. Rep. of Germany

[21] Appl. No.: 207,766

[22] Filed: Jun. 16, 1988

[30] Foreign Application Priority Data

Jun. 19, 1987 [DE] Fed. Rep. of Germany ....... 3720245

[51] Int. Cl.$^5$ .......................................... C07C 101/44
[52] U.S. Cl. ...................................... 560/43; 560/36; 562/433; 562/441; 562/455; 562/456; 562/457
[58] Field of Search .................... 560/36, 43; 562/433, 562/441, 455, 456, 457

[56] References Cited

U.S. PATENT DOCUMENTS 4,182,624  1/1980  Soeder et al. ........................ 71/92

FOREIGN PATENT DOCUMENTS 0207563  1/1987  European Pat. Off. .
3515094  10/1986  Fed. Rep. of Germany .

OTHER PUBLICATIONS

Eggensperger et al., *Chemical Abstracts*, vol. 81, No. 3383k, (1974).

"Synthesis of Strombine, a New Method for Monocarboxymethylation of Primary Amines", Jan Kihlberg, Rolf Bergman and Boerje Wickberg, Acta Chemica Scandinavica B 37 (1983), pp. 911–916.

*Primary Examiner*—Bruce D. Gray
*Attorney, Agent, or Firm*—Curtis, Morris & Safford

[57] ABSTRACT

The invention relates to a process for the preparation of compounds of the formula I

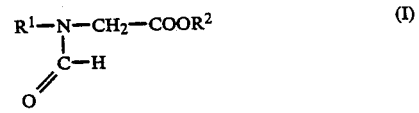

in which $R^1$ denotes (substituted) aryl or (substituted) cyclohexyl and $R^2$=alkyl, in which a compound of the formula $R^1$—$NH_2$ is reacted with at least twice the molar amount of glyoxylic acid in the presence of water and the resulting acid is then esterified.

8 Claims, No Drawings

PROCESS FOR THE PREPARATION OF N-ALKOXYCARBONYLMETHYL-N-FORMYL-AMINES AND -ANILINES

DESCRIPTION

The present application relates to a process for the preparation of N-alkoxycarbonylmethyl-N-formyl-amines and -anilines.

N-Alkoxycarbonylmethyl-N-formylamines and -anilines are useful intermediates of 1-substituted imidazole-5-carboxylic acid derivatives which have both a pharmacological and biocidal activity (see, for example, German Offenlegungsschrift 2,732,531, German Offenlegungsschrift 3,217,094, German Offenlegungssschrift 3,444,918, German Offenlegungsschrift 3,514,116, U.S. Patent 3,485,917 and European Patent Application 207,563).

The customary synthesis of these compounds such as is described, for example, in German Offenlegungsschrift 2,732,531, German Offenlegungsschrift 3,515,094 or European Patent Application 207,563 leads to the compounds mentioned either by alkylation of the amine-aniline with halogenoacetic acid esters and subsequent N-formylation or by primary N-formylation and subsequent amidoalkylation with halogenoacetic acid esters.

A novel process has now been found in which an amine or aniline is reacted with aqueous glyoxylic acid and the resulting acid is then esterified.

In comparison with the known processes, the novel process has several advantages:

The use of irritating halogenoacetic acid ester derivatives can be dispensed with.
No organic or inorganic auxiliary bases (alkylation stage of the known processes) are required;
Only carbon dioxide is formed as a by-product.

The reaction of amines with glyoxylic acid and subsequent hydrolysis of the formyl group to give N-alkyl-substituted glycine derivatives is described by J. Kihlberg el al. in Acta Chem. Scand. B 37 (1983) 911–6. However, the authors use glyoxylic acid hydrate as the reaction component and refer to marked inhibition of the reaction in the presence of water. Surprisingly, however, the process can be carried out with substantially cheaper aqueous glyoxylic acid.

The invention thus relates to a process for the preparation of the compounds of the formula I $$R^1-N-CH_2-COOR^2 \quad (I)$$
$$\underset{O}{\overset{|}{C}}-H$$

in which
$R^1$ denotes one of the radicals of the formulae m denotes 0, 1, 2, 3 or 4,
n independently of one another denote 0, 1 or 2
$R^2$ denotes $(C_1-C_6)$-alkyl,
$R^3$ independently of one another denote $(C_1-C_3)$-alkyl, halogen or $(C_1-C_4)$-alkoxy;
$R^4$ independently of one another denote $(C_1-C_3)$-alkyl and
$R^5$ denotes hydrogen, $(C_1-C_4)$-alkyl, phenyl or cyclohexyl, which comprises (a) reacting an amine of the formula II with at least twice the molar amount of aqueous $$R^1-NH_2 \quad (II)$$

$$R^1-N-CH_2-COOH \quad (III)$$
$$\underset{O}{\overset{|}{C}}-H$$

glyoxylic acid to give the carboxylic acid of the formula III and (b) subsequently esterifying this with an alcohol of the formula $R^2OH$.

In relation to the process according to the invention, the following radicals are preferred for $R^1$:

Halogen is preferably understood as being chlorine or bromine. If the compounds of the formula I have at least one optically active center, the preparation process relates to all the optical isomers or mixtures thereof.

At least 2.0 times the molar amount, preferably 2.0–3.0 times the molar amount, of glyoxylic acid (based on II) is required for the preparation of the carboxylic acid III formed as the intermediate, in order to achieve complete conversion of the amine or aniline. The water content of the glyoxylic acid can vary between 30% by weight and 80% by weight, it advantageously being possible for a technical grade glyoxylic acid solution (about 40–60% by weight of water) to be used.

The temperatures in process step (a) can vary between 0° C. and 150° C., depending on the solvent used, the step preferably being carried out between 20° C. and 120° C. The progress of the reaction can easily be recognized from the evolution of the gas.

Process step (a) can be carried out without or advantageously in the presence of an organic solvent which is as far as possible water-miscible, such as, for example, ethanol, dimethylformamide or formic acid, particularly advantageously in the presence of formic acid.

The acid of the formula III formed as the intermediate can be either isolated, for example by taking up the reaction mixture in water and filtering off the reaction product with suction or extracting it or by evaporating off the solvent and crystallizing the residue, or esterified—advantageously after evaporating off the solvent—directly with an alcohol of the formula $R^2OH$.

The esterification of the carboxylic acid of the formula III can be carried out by customary methods (see, for example, Organikum, VEB Deutscher Verlag der Wissenschaften, Berlin 1973, pages 440–443).

The yields after carrying out the two reaction steps (a) and (b) are good to very good and are about 60–95% of theory, depending on the amine or aniline.

The following examples serve to illustrate the invention further.

PREPARATION EXAMPLES

EXAMPLE 1

Methyl 2,6-diethyl-N-formyl-anilino-acetate 32.6 g (0.22 mole) of an approximately 50% strength aqueous glyoxylic acid solution were added dropwise to 14.9 g (0.10 mole) of 2,6-diethylaniline and 100 ml of formic acid at room temperature, with gentle warming. The mixture was stirred at 70° C. for 1 hour, with vigorous evolution of gas, the formic acid was distilled off up to an internal temperature of 120° C., the mixture was allowed to cool and was poured onto water and the solid was filtered off with suction and dired. 21.8 g of N-(2,6-diethylphenyl)-N-formylglycine of melting point 139–41° C. were obtained.

The solid was taken up in 50 ml of methanol, 2 ml of concentrated sulfuric acid were added and the mixture was heated under reflux for 5 hours. After cooling, the reaction mixture was taken up in water and the product was extracted with toluene. The organic phase was evaporated and the residue was distilled under a high vacuum. 19.5 g (78% of theory with respect to the aniline used) of methyl 2,6-diethyl-N-formylanilinoacetate (boiling point 126–9° C./0.5 mbar) were obtained.

EXAMPLE 2

Ethyl 2,6-diethyl-N-formyl-anilino-acetate 74.5 g (0.50 mole) of 2,6-diethylaniline were reacted with 185 g (1.25 mole) of an approximately 50% strength aqueous glyoxylic acid solution in 500 ml of formic acid analogously to Example 1. After the formic acid had been distilled off, 500 ml of chloroform, 200 ml of ethanol and 1 ml of concentrated sulfuric acid were added and the mixture was distilled, using a water separator, until the formation of water had ended. The mixture was allowed to cool and was evaporated and the residue was distilled under a high vacuum. 109 g of ethyl 2,6-diethyl-N-formylanilino-acetate (83% of theory) were obtained as a pale yellow oil of boiling point 145–7° C./0.5 mbar.

EXAMPLE 3

Ethyl N-formyul-2,6-diethyl cyclehexylamino-acetate 15.5 g (0.10 mole) of 2,6-diethylcyclohexylamine were heated at 100° C. with 32.6 g (0.22 mole) of 50% strength aqueous glyoxylic acid solution in 100 ml of formic acid for 2 hours. The formic acid was distilled off under a slight vacuum, the residue was poured into water and the solid which had precipitated was filtered off with suction and dried. 18.9 g of acid of melting point 125–130° C. were obtained. For the esterification, 100 ml of anhydrous ethanol were added and hydrogen chloride gas was passed in under reflux for 7 hours. After cooling, the mixture was evaporated and the residue was chromatographed over a silica gel column (mobile phase petroleum ether (low-boiling): ethyl acetate $=7:3$). 17.0 g (66% of theory with respect to the amine used) of ethyl N-formyl-2,6-diethylcyclohexylamino-acetate were obtained as a colorless oil. Identification was by $^1$H-NMR spectroscopy.

EXAMPLE 4

Ethyl N-formyl-benzyhydrylamino-acetate 29.7 g (0.16 moles) of benzhydrylamine were stirred with 59.7 g (0.40 mole) of a 50% strength aqueous glyoxylic acid solution in 160 ml of formic acid at 100° C. for 8 hours. The excess formic acid was distilled off, the mixture was allowed to cool and was poured into water and extracted with ethyl acetate and the organic phase was dried over sodium sulfate and evaporated. After addition of 200 ml of absolute ethanol and 4.4 g of concentrated sulfuric acid, the mixture was stirred under reflux for 5 hours, allowed to cool and evaporated, the residue was taken up in 2 N sodium hydroxide solution/toluene, the organic phase was dried and evaporated and the residue was chromatographed (silica gel; mobile phase: petroleum ether (low-boiling) : ethyl acetate $=8:2$). 26.6 g (56% of theory) of ethyl N-formyl-benzhydrylamino-acetate was obtained as a colorless oil. Identification was by $^1$H-NMR spectroscopy.

EXAMPLE 5

Ethyl N-formyl-1-tetralinylamino-acetate 27.6 g (0.19 mole) of 1-aminotetralin were heated at 150° C. with 70.3 g (0.48 mole) of a 50% strength aqueous glyoxylic acid solution in 185 ml of formic acid for 2 hours. The excess formic acid was distilled off, the residue was poured into water and the solid was filtered off with suction (35.2 g of acid of melting point 135–140° C.). After addition of 150 ml of anhydrous ethanol and 2.6 g of concentrated sulfuric acid, the mixture was stirred under reflux for 6 hours and evaporated, the residue was taken up in 2 N sodium hydroxide solution/toluene, the toluene phase was dried with sodium sulfate and evaporated and the residue was chromatographed (silica gel; petroleum ether (low-boiling): ethyl acetate $=7:3$). 31.4 g (63% of theory) of ethyl N-formyl-1-tetralinylamino-acetate were obtained as a pale yellow oil. Identification was by $^1$H-NMR spectroscopy.

Further examples are shown in the following Table 1.

$$R^1-N(-CHO)-CH_2-COOR^2 \quad \text{I}$$

| Example No. | R¹ | R² | (R³)ₘ |
|---|---|---|---|
| 6 | phenyl with R³ substituent | $C_2H_5$ | 2,6-dimethyl |
| 7 | " | " | 2-ethyl-6-methyl |
| 8 | " | " | 2,6-diethyl, 3-Cl |
| 9 | " | " | 2,6-diethyl, 3-Br |
| 10 | " | " | 2,6-diethyl, 3-Cl-4-methyl |
| 11 | " | $n\text{-}C_4H_9$ | 2,6-diethyl, 3,5-dichloro |
| 12 | " | $C_2H_5$ | 2-chloro-6-methyl, 4-Cl |
| 13 | " | " | 2-butoxy-6-methyl |
| 14 | " | " | 2,6-diisopropyl |
| 15 | 1-phenylethyl (CH(CH₃)-phenyl) | $CH_3$ | |
| 16 | α-cyclohexyl-benzyl (CH(H)-cyclohexyl attached to phenyl) | $C_2H_5$ | |
| 17 | tetrahydronaphthyl (with (R⁴)ₘ) | $C_2H_5$ | 2-methyl |
| 18 | " | " | 2,2-dimethyl |
| 19 | " | " | 2-ethyl |
| 20 | " | " | 2,4-dimethyl |
| 21 | " | " | 2,2,4-trimethyl |
| 22 | 5,8-dimethyl-tetrahydronaphthyl | " | H |
| 23 | " | " | 2,2-dimethyl |
| 24 | indanyl (with (R⁴)ₘ) | " | H |
| 25 | " | " | 2-methyl |
| 26 | " | " | 2-ethyl |
| 27 | " | " | 2,2-dimethyl |
| 28 | fluorenyl-type bicyclic | $C_2H_5$ | — |
| 29 | dihydroanthracenyl-type tricyclic | " | — |

We claim:

1. A process for the preparation of compound of the formula I $$R^1-N(\overset{\underset{\|}{C(=O)H}}{})-CH_2-COOR^2$$

in which

R¹ is a radical of the formula

[phenyl with (R³)ₘ], [cyclohexyl with (R⁴)ₘ and H], [benzyl-type with R⁵],

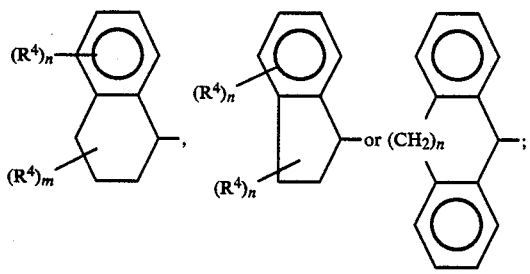

m is 0, 1, 2, 3 or 4;
n independently of one another area 0, 1 or 2;
$R^2$ is $(C_1-C_6)$-alkyl;
$R^3$ independently of one another are $(C_1-C_3)$-alkyl, halogen or $(C_1-C_4)$-alkoxy;
$R^4$ independently of one another are $(C_1-C_3)$-alkyl; and
$R^5$ is hydrogen, $(C_1-C_4)$-alkyl, phenyl or cyclohexyl, which comprises (a) reacting an amine of the formula II with at

   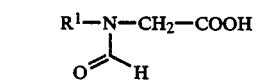

II   III least twice the molar amount of glyoxylic acid in the form of a 30 to 80% strength aqueous solution to give the carboxylic acid of the formula III and b) subsequently esterifying the carboxlyic acid of the formula III with an alcohol of the formula $R^2OH$.

2. The process for the preparation of a compound of the formula I as claimed in claim 1, wherein
$R^1$ is a radical of the formula

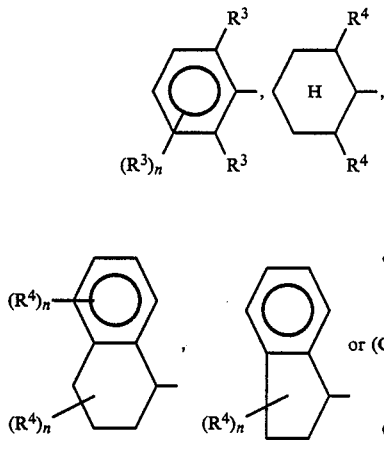

n independently of one another are 0, 1 or 2;
$R^2$ is $(C_1-C_6)$-alkyl;
$R^3$ independently of one another are $(C_1-C_3)$-alkyl, halogen or $(C_1-C_4)$-alkoxy; and
$R^4$ independently of one another are $(C_1-C_3)$-alkyl.

3. The process as claimed in claim 1, wherein 2.0 to 3.0 times the molar amount of glyoxylic acid, based on component II, is used in the form of a 30 to 80% strength aqueous solution.

4. The process as claimed in claim 1, wherein glyoxylic acid is used in the form of a 40 to 60% strength solution.

5. The process as claimed in claim 1, wherein the reaction temperature in process step (a) is 0° C. to 150° C.

6. The process as claimed in claim 1, wherein the reaction temperature in process step (a) is 20° C. to 120° C.

7. The process as claimed in claim 1, wherein process step (a) is carried out in the presence of an organic solvent.

8. The process as claimed in claim 7, wherein formic acid is used as the solvent in process step (a).

* * * * *